United States Patent [19]

Pier et al.

[11] 4,285,936

[45] Aug. 25, 1981

[54] METHOD FOR PRODUCING A VACCINE AGAINST BACTERIAL INFECTIONS CAUSED BY *PSEUDOMONAS AERUGINOSA*

[75] Inventors: Gerald B. Pier, Brookline, Mass.; Jerald C. Sadoff, Washington, D.C.

[73] Assignee: The United States of America as represented by the Secretary of the Army, Washington, D.C.

[21] Appl. No.: 101,620

[22] Filed: Dec. 10, 1979

[51] Int. Cl.$^3$ .................... A61K 31/70; C08B 37/00; A61K 39/104

[52] U.S. Cl. .................................. 424/180; 424/88; 424/92; 536/1

[58] Field of Search ................ 424/92, 88, 180; 536/1

[56] References Cited

PUBLICATIONS

Pier, G., et al., Injection and Immunity, vol. 22, pp. 908–925, 1978.

*Primary Examiner*—Johnnie R. Brown
*Assistant Examiner*—Blondel Hazel
*Attorney, Agent, or Firm*—William G. Gapcynski; Werten F. W. Bellamy; Sherman D. Winters

[57] ABSTRACT

A method for isolating a non toxic, high molecular weight polysaccharide antigen from the crude slime of a *Pseudomonas aeruginosa* culture, and a method for inducing immunity in a host to said live organisms is described. The slime is initially prepared for the isolation procedure by separating the bacterial cells from the slime and dissolving the slime in a phosphate buffer solution. Dissolved contaminating nucleic acids are then precipitated and separated from solution. A lipid A portion of the contaminating lipopolysaccharide constituent is then removed and precipitated by acetic acid hydrolysis, and the remaining lipids present are extracted with chloroform. Nearly all of the residual nucleic acids are then removed by digestion with nucleases, and the remaining protein extracted with phenol. The aqueous and phenol layers are then separated, and the aqueous layer applied to a gel filter to isolate the antigen by column chromatography. The antigen appears in the void volume. A vaccine containing the polysaccharide antigen of this invention has been successfully tested and found to be non toxic and highly effective in inducing an immune response to the organism in a host.

5 Claims, No Drawings

METHOD FOR PRODUCING A VACCINE AGAINST BACTERIAL INFECTIONS CAUSED BY *PSEUDOMONAS AERUGINOSA*

The invention relates to a method for producing a vaccine to induce immunity in a host to gram negative bacteria and specifically to *Pseudomonas aeruginosa*. In particular, this invention relates to the discovery that a non toxic high molecular weight polysaccharide (hereinafter PS) can be isolated from the crude slime of cultures of said bacteria.

The PS antigen of this invention has been found effective to induce immunity in mice, and has been found to be non pyrogenic when tested in rabbits.

Death from septicemic *P. aeruginosa* remains a major problem for the compromised host. Studies in animals and humans have suggested that immunization with either killed organisms or purified bacterial antigens has some efficacy in reducing the incidence of mortality associated with this bacterial infection. Recently a heptavalent lipopolysaccharide (hereinafter LPS) from strains of *P. aeruginosa* was isolated and tested in burn patients, patients with malignancies, and children with cystic fibrosis.

These trials however, did not provide statistically significant results in reducing the incidences of infections with the immunized group. Most importantly however, vaccination with this preparation was associated with a high incidence of side effects, especially in children, therefore limiting its use.

While safe and effective vaccines have been prepared for a number of pathogenic bacteria, there remains a need for such a vaccine relative to *P. aeruginosa*. Infections by this bacteria occur principally in burned patients, cancer patients having suppressed immunity due to thereapy, or in patients traumatized by a major surgery. The infection manifests itself in shock, vascular collapse, a drop in urinary output and lesions of necrotic skin. Such infections are often fatal. The infections are commonly treated with antibiotics, but even with antibiotic treatment mortality is high. In the case of immuno-suppressed cancer patients, the infection is nearly always fatal.

A treatment with antibiotics, as is well known, is very expensive. In addition, the organism continues to develop resistance as new antibiotics are developed. Development of a vaccine however, would improve the body defenses to invasion by the bacteria. In addition, bacterial infection in a high risk patient, such as a burned patient, often will set in about two weeks after the trauma. There is therefore time for developing an immune response to a vaccine after the trauma.

Safe and effective vaccines have been prepared from high molecular weight polysaccharide capsules from a number of pathogenic bacteria. It has now been discovered that a high molecular weight polysaccharide antigen can be isolated from the crude slime of *P. aeruginosa* strains, which is non toxic and non pyrogenic and highly effective in inducing an immune response in the host.

The isolation procedure of this invention depends upon removal of contaminating constituents of the crude slime. The bacterial cells are removed initially, and the contaminating nucleic acids precipitated. The lipopolysaccharide constituent is then subjected to acetic acid hydrolysis and lipids removed by extraction. Then following extraction of residual nucleic acids and proteins, the antigen of this invention is isolated by column chromatography.

The antigen of this invention will not bind to ion exchange resins.

The PS of this invention has been found to be effective in mice, and upon successive injections thereof has been found 100% effective against lethal dosages of the live organism.

Accordingly, it is an object of this invention to provide a method for isolating a non toxic antigen from live cultures of *P. aeruginosa*.

It is another object of this invention to isolate a high molecular weight polysaccharide from said cultures which will induce immunity in a host to lethal challenge by said organism.

It is yet another object of this invention to induce immunity in a host to challenges by *P. aeruginosa*, by successive injections of a high molecular weight polysaccharide constituent of the crude slime from live cultures of said organism.

It is still a further object of this invention to isolate a high molecular weight polysaccharide antigen from the crude slime *P. aeruginosa* cultures, by removing the nucleic acid constituents, acetic acid hydrolysis, followed by extraction to remove the lipids, and subsequently isolation of the antigen by column chromatography.

These and other objects will become readily apparent with reference to the following description:

In order to isolate the antigen of this invention for evaluation, a culture of *P. aeruginosa*, Fisher-Devlin immunotype 1 (No. 05139) was maintained on trypticase soy ager (TSA) slants at 4° C. and transfers are made every two months.

The crude slime was prepared based on the method of Alms et al *J. Infect. Dis.* 117: 249-256.

The preparation from a solid culture utilized 500 ml of TSA with 3% glycerin in diphtheria toxin bottles which were inoculated with 10 ml of a four hour culture of *P. aeruginosa* grown in trypticase soy broth (TSB) and incubated at 37° C. for 48-72 hours. After this growth period, 25-50 ml of saline was added to each bottle and the growth washed off with the aid of a glass scraper.

The saline solution was poured off and combined from each bottle, and the suspended cells stirred with a magnetic bar for 3-24 hours at 4° C. The cells were then removed by centrifugation and the supernate, after passage through a 0.45μ filter, slowly diluted with 95% ethanol with stirring at 4° C. until the alcohol concentration was 80%. The resulting precipitate was collected by centrifugation, resuspended in phosphate buffered saline of pH 7.2 and designated crude slime from solid cultures. Phosphate buffered saline (hereinafter PBS) has a concentration of 6.8 grams NaCl, 1.48 grams $Na_2HPO_4$, 0.43 grams $KH_2PO_4$ per liter).

Material from liquid cultures was prepared by inoculating 1 liter amount of TSB with 3% glycerine in 4 liter flasks with 10 ml of a 4 hour TSB culture and incubating at 37° C. for 48-72 hours. Cells were removed by centrifugation and the media supernate concentrated to one-tenth the volume in a rotary evaporator. The pelletted cells were resuspended in PBS and dispersed by high speed in an Omnimixer for 10 minutes. This slurry was centrifuged to remove cells, and the supernate added to the concentrated culture media. Ethanol (95%) was then added to a concentration of 30%, and the liquid centrifuged to remove precipitated nucleic acids and cells. The alcohol concentration was then raised to 80% and the resulting precipitate collected by centrifugation. The pelletted material was redissolved in PBS and designated crude slime from liquid culture.

In the alternative, prior to centrifuging to remove the organisms, 0.5% by weight/volume of cetavalon (cetyltrimethylammonium bromide) may be added. The cetavalon will cause precipitation of nucleic acids which are then removed with the organism cells by centrifugation.

Also in the alternative, in lieu of a rotary evaporation concentration step, the solution may be put through a series of fifteen ultra filters. The ultra filters are commercially available by, for example, AMICON Corporation, and preferably utilize a 30,000 exclusion limit to produce the volume needed.

The polysaccharide antigen may be isolated as follows:

If cetavalon was not utilized prior to removal of the live organisms, a 10% cetavalon solution is added to the dissolved crude slime to a final concentration of 1% and allowed to stand at room temperature for 30 minutes to precipitate nucleic acids. Following centrifugation, 95% ethanol is added to the supernate to a final concentration of 80% and the resultant precipitate collected by centrifugation and redissolved in PBS. The cetavalon and alcohol precipitation steps are then repeated.

After the second alcohol precipitation and centrifugation the collected pellet is dissolved in 1% acetic acid at a concentration of approximately 5 mg/ml, and heated at 90° C. for 18 hours to cleave off and precipitate the lipid A portion of the continimating lipid polysaccharide (hereinafter LPS). After cooling, the precipitated lipid is removed by centrifugation and the acetic acid supernate extruded 5-10 times with chloroform to remove residual lipids presents. When there is no longer a precipitate at the interface of the aqueous and organic layers, the PS is precipitated from the aqueous layer by alcohol precipitation, collected by centrifugation and redissolved in PBS (10 mg/ml).

Residual nucleic acids are then removed by digestion with nucleases. RNase is added to the solution at a final concentration of 0.05 mg/ml, and $MgSO_4$, 0.1 M final concentration, is also added, and the mixture incubated at 37° C. for an additional 4 hours. The remaining protein is then removed by treatment with an equal volume of 90% phenol. After vigorous mixing, the solution is cooled and maintained at 4° C. for a minimum of 12 hours. The aqueous and phenol layers are then separated by centrifugation and, after removal of the water layer, PS is precipitated from the water layer by the addition of alcohol to 80% (v/v), and collected by centrifugation. The PS is redissolved in PBS (5-7 ml) and applied to a 2.6×100 cm column of Sephadex G-100 equilibrated in PBS (flow rate of 30 ml per hour). The eluate is monitored at wavelengths of 206 nm and 254 nm. The void volume fractions are combined and the PS precipitated by the addition of alcohol to 80% (v/v). The collected pellet is redissolved in water and desalted on a 1.5×60 cm column of Sephadex G-50 equilibrated with distilled water. The void volume from this column is collected and lyophilized.

For the purposes of analysis, the lipopolysaccharide (LPS) constituent was isolated also, and the lipid A and what was found to be a polysaccharide side chain from LPS were also isolated.

LPS was purified by either phenol-water extraction of whole cells by the method of *Westphal Z. Naturforish* 79 148-155, or from crude slime as follows: crude slime or concentrated liquid culture supernates were ultra-centrifuged at 105,000×G for 3 hours, the pellet resuspended in PBS and ultra-centrifuged again under the same conditions. The pellet was then resuspended in PBS and digested with nucleases under the same conditions as the PS. After DNase treatment, the mixture was digested with Pronase B (1 mg/ml) at 37° C. for 24 hours. This material was then applied to a 2.6×100 cm column of Sepharose 4B (flow rate 30 ml per hour) and fractions eluting as the void volume combined, precipitated with alcohol, collected by centrifugation, dialyzed and lyophilized.

To isolate the lipid A and polysaccharide side chains LPS was treated with 1% acetic acid (2.5 mg/ml) at 90° C. for 18 hours to cleave off the lipid A moiety. The lipid A precipitate was removed by centrifugation washed three times with distilled water and lyophilized. The acetic acid supernate was extracted three times with chloroform and then applied to a 2.6×100 cm column of Sephadex G-100 equilibrated in PBS (flow rate 30 ml per hour). The eluate was monitored at 206 nm and 256 nm and the peak fractions combined, precipitated with alcohol (80% v/v), resuspended in water, dialyzed and lyophilized.

The chemical composition of PS and LPS constituents were evaluated utilizing standard techniques of analyses. The PS antigen was composed primarily of carbohydrate and water. No lipid, phospherous, heptose, protein, or 2-Keto-3-Deoxyoctonate (KDO) could be detected, and nucleic acid contamination was generally at a level of 1-2%. The LPS contained protein, lipid, carbohydrate, phosphorous, and a higher amount of contaminating nucleic acid. Table 1 below summarizes thses findings.

Quantitative and qualitative assay of carbohydrates and lipids performed by gas liquid chromatography as shown on Table 2 below were used to evaluate PS, intact LPS and the acetic acid hydrolized polysaccharide portion of LPS.

The lipid content of LPS was also evaluated, and six major fatty acids were found with 2-hydroxy-dodecanoic acid and 3-hydroxy-dodecanoic acid accounting for 69% on a molar basis. Furthermore, the 18 carbon fatty acid was found to contain a single double bond on the basis of its eluting from the gas liquid chromatographic column ahead of octadecanoic acid and having a molecular ion of 297 by mass spectroscopy (molecular ion of octadecanoic acid equals 299).

TABLE 1

| Chemical composition[1] of the PS and LPS from immunotype 1 *P. aeruginosa* | | |
|---|---|---|
| Component | PS | LPS |
| Carbohydrate | 75[2] | 80 |
| Lipid | 0.0 | 10.5 |
| Nucleic acid | 1.0 | 1.6 |
| Protein | 0.0 | 4.3 |
| Phosphate[3] | 0.0 | 2.8 |
| Water | 21.7 | ND |
| Total | 97.7 | 99.2 |

[1]Average of three lots.
[2]Weight percent
[3]Phosphate values determined after material passed over a DEAE-Sephadex A-50 column in 0.1M NaCl to remove last traces of nucleic acids.
[4]ND — not determined

TABLE 2

Molar ratios of sugars composing the PS and LPS of immunotype 1 *P. aeruginosa*

| Preparation | ara[1] | rham | man | gal | glu | KDO | gluam | galam | Hep | Dideoxy gal |
|---|---|---|---|---|---|---|---|---|---|---|
| lots 1–5 combined | 0.07 | 0.65 | 0.16 | 0.32 | 1.0 | 0 | 0 | 0 | 0 | 0 |
| lot 8 | 0.02 | 0.66 | 0.05 | 0.33 | 1.0 | 0 | 0 | 0 | 0 | 0 |
| lot 10 | 0.03 | 0.66 | 0.10 | 1.08 | 1.0 | 0 | 0 | 0 | 0 | 0 |
| liquid culture | 0.10 | 0.23 | 0.30 | 0.01 | 1.0 | 0 | 0 | 0 | 0 | 0 |
| intact LPS | 0 | 0.95 | 0.04 | 0 | 1.0 | 0.06 | 0.20 | 0.20 | 0.10 | ++[2] |
| polysaccharide from LPS[3] | 0 | 0.04 | 0.04 | 0 | 1.0 | 0 | 0 | 0 | 0 | 0 |

[1] ara, arabinose; rham, rhamnose; man, mannose; gal, galactose; glu, glucose; KDO, 2-keto-3-deoxy actonoate; gluam, 2-acetamide-2-deoxy glucose; galam, 2-acetamido-2-deoxy galactose; Hep, L-glycero-D-manno-heptose; dideoxy gal, 2-acetamido-2,6-dideoxy galactose.
[2] Lack of a standard prohibits assignment of a molar value.
[3] Polysaccharide obtained from LPS hydrolyzed for 18 h at 90° C. with 1% acetic acid and then subjected to column chromatography. Void volume peak, second peak, and third peak analyzed here.

The PS antigen was found to have a molecular weight of between 350,00 and 100,00 daltons. In addition, attempts to bind PS to ion exchange resins under a variety of conditions were uncessessful. This property did allow for the removal of the last traces of nucleic acid on a DEAE-Sephadex A-50 column in 0.01 M NaCl.

In summary then, the PS antigen of this invention was found to be composed of polymers of a heterogenous size between 350,000 and 100,000 daltons. It is free of detectable lipid, protein, and KDO, has a level of nucleic acid contamination, and is composed of rhamnose, glucose, galactose, arabinose, and mannose. The antigenic determinants of PS were found to be relatively acid stable (1% acetic acid for up to 72 hours at 90° C.) but very alkali labile (0.1 NaOH for 1 hour at 37° C.). The PS antigen could only be purified free from LPS by hydrolysis of contaminating LPS into its lipid and polysaccharide portions with subsequent removal of these products.

Acetic acid hydrolysis of purified LPS was found to yield a product immunologically indistinguishable from PS, but also elutes as the void volume G-100 column. PS preparations then contain this material to a variable degree. The product of acetic acid hydrolysis of LPS may represent a high molecular weight O-side chain of *P. aeruginosa* LPS. This has not been conclusively established however.

However, the lack of toxicity and pyrogenicity of PS in mouse and rabbit tests was found to be in marked contrast to that of LPS. Because attempts to immunize humans with heptavalent LPS vaccine were hampered by the toxicity of this preparation, the isolation of a non toxic, high molecular weight polysaccharide from the slime of *P. aeruginosa* according to the method of this invention will eliminate the prior art problems associated with attempts to immunize with LPS vaccine.

IMMUNIZATION EVALUATION

Two to four week old outbred ICR mice, weighing 12 to 17 grams at the time of immunization and 22 to 30 grams at the time of challenge were obtained from an animal colony and employed to evaluate effectiveness of the polysaccharide of this invention. Mice were immunized by either intraperitoneal (IP), subcutaneous (SubQ), or intravenious (IV) injections with 0.1 ml of the antigen in saline. Seven days later all challenges were performed by IP inoculation of the appropriate dose of live organisms in 0.1 ml of saline. Challenge doses were prepared from 18 hour cultures of *P. aeruginosa* immunotype 1 grown on TSA with 3% glycerol at 37° C. and suspended in saline to an optical density of 1.2 at 650 nm. Mice were observed for 96 hours. The 50% lethal dosage ($LD_{50}$) values were determined from the results of IP administration of graded doses of live organisms and calculated by the method of Reed et al *Am.J.HYG.* 27: 493–497. Variability of the $LD_{50}$ value of a given dose necessitated a separate $LD_{50}$ determination for each different immunization-challenge experiment.

Table 3 below shows the results of two experiments immunizing mice with varying amounts of PS by the IV route and subsequent challenge. A dose of 10–25 ug per mouse was needed to afford a protection level of 60–70%. All non-immunized mice given an equivalent challenge dose in this and all subsequent experiments were dead by 24 hours post challenge. Higher doses of PS did not increase the protection level beyond 70%, but protective levels of 100% were achieved if two immunizing doses were given five days apart, with challenge seven days after the second immunization. Also, challenging mice with 5 $LD_{50}$ units required only 0.1 ug of PS antigen for 70% protection while still killing 90% of the control mice.

In order to show that PS was not non-specifically activating an inflammatory response in the peritoneum of the immunized mice, the animals were inoculated with PS Sub Q on the back of the neck or IV in the tail vein and then challenged IP. These routes of immunization elicited 90–100% protection against 30 $LD_{50}$ units as shown on Table 5 below.

TABLE 3

Protection of mice by IP immunization with PS and IP challenge with IT-1 *P. aeruginosa*

| Amount PS given (ug) | Challenge dose ($LD_{50}$) | No. of organisms | No. Survivors Total | % Protection |
|---|---|---|---|---|
| 100 | 30 | $1.0 \times 10^8$ | 6/10 | 60 |
| 50 | " | " | 6/10 | 60 |
| 25 | " | " | 7/10 | 70 |
| 10 | " | " | 6/10 | 60 |
| 0 | " | " | 0/10 | 0 |
| 100 | 50 | $1.7 \times 10^8$ | 8/10 | 80 |
| 50 | " | " | 8/10 | 80 |
| 25 | " | " | 6/10 | 60 |
| 10 | " | " | 5/10 | 50 |
| 1 | " | " | 2/10 | 20 |

TABLE 3-continued

Protection of mice by IP immunization with PS and IP challenge with IT-1 P. aeruginosa

| Amount PS given (ug) | Challenge dose (LD$_{50}$) | No. of organisms | No. Survivors Total | % Protection |
|---|---|---|---|---|
| 0 | " | " | 0/10 | 0 |

Mice were given the indicated amount of antigen of 0.1 ml of saline IP and challenged 7 days later with the indicated number of organisms in 0.1 ml of saline IP.

TABLE 4

Protection of Mice to Low Dose Challenge With IT-1 P. aeruginosa After Immunization With PS

| Amount PS given (ug) | Challenge dose (LD$_{50}$) | No. of organisms | No. survivors Total | % Protection |
|---|---|---|---|---|
| 10 | 5 | $1.7 \times 10^7$ | 8/10 | 80 |
| 1 | " | " | 10/10 | 100 |
| 0.5 | " | " | 9/10 | 90 |
| 0.1 | " | " | 7/10 | 70 |
| 0 | " | " | 1/10 | 10 |

Mice were immunized IP with the antigen in 0.1 ml of saline and challenged IP 7 days later with the indicated number of organisms in 0.1 ml saline.

TABLE 5

Protection of mice by SubQ and IV immunization with PS against IP Challenge with IT-1 and IT-4 P. aeruginosa

| Amount PS given (ug) | Route | Challenge dose (LD$_{50}$) | No. of organisms | No. survivors Total | % Protected |
|---|---|---|---|---|---|
| 50 | Sub Q | IT-1(8) | $8.0 \times 10^7$ | 9.10 | 90 |
| 50 | IV | " | " | 10/10 | 100 |
| 0 | Sub Q | " | " | 0/10 | 0 |
| 0 | IV | " | " | 0/10 | 0 |
| 50 | Sub Q | IT-4(5) | $6.0 \times 10^7$ | 0/10 | 0 |
| 50 | IV | " | " | 0/10 | 0 |

Mice were immunized with the antigen in 0.1 ml of saline by the indicated route and challenged 7 days later IP with the indicated number of organisms in 0.1 ml saline.

Further evidence that a specific immune response had occurred in the immunized mice was shown by the inability of the immunized mice to survive challenge with a low amount of immunotype 4 P. aeruginosa organisms, as also shown on Table 5.

LPS was next tested as an immunogen and the results of two experiments are shown in Table 6 below. LPS was much more immunogenic on a weight basis than PS, with as little as 0.001 ug of LPS giving 87.5% protection in one of the experiments. In order to ensure that LPS contamination might not be the cause of protection seen with PS immunizations, and in view of the fact that alkali treated PS has been found to loose all serological activity, whereas alkali treated LPS retained some activity, mice were immunized with alkali treated PS or alkali treated LPS. Table 7 below shows the results. Alkali treated PS could not induce protection in mice, whereas alkali treated LPS remained able to induce 90-100% protection.

Because a polysaccharide antigen had been isolated from LPS by acetic acid hydrolysis and column chromatography and this antigen was found to be immunologically identical to PS, but different from PS by a lack of galactose and arabinose, mice were immunized with this antigen to judge its ability to confer protection. Immunization of mice with with polysaccharide portion of LPS that eluted as the void volume of a G-100 column induced protective levels of 70% against challenge of $1.5 \times 10^9$ organisms.

TABLE 6

Protection of mice by IP immunization with LPS against IP challenge with IT-1 P. aeruginosa

| Amount LPS given (ug) | Challenge doses (LD$_{50}$) | No. of organisms | No. survivors Total | % Protected |
|---|---|---|---|---|
| 0.5 | 30 | $1.5 \times 10^9$ | 9/10 | 90 |
| 0.1 | " | " | 9/10 | 90 |
| 0.05 | " | " | 9/10 | 90 |
| 0.01 | " | " | 7/10 | 70 |
| 0.005 | " | " | 4/10 | 40 |
| 0.001 | " | " | 0/10 | 0 |
| 0 | " | " | 0/10 | 0 |
| 1.0 | 10 | $1.2 \times 10^8$ | 8/8 | 100 |
| 0.5 | " | " | 8/8 | 100 |
| 0.1 | " | " | 8/8 | 100 |
| 0.05 | " | " | 8/8 | 100 |
| 0.01 | " | " | 7/8 | 87.5 |
| 0.001 | " | " | 7/8 | 87.5 |
| 0 | " | " | 0/8 | 0 |

Mice were immunized with indicated amounts of LPS in 0.1 ml of saline IP and challenged 7 days later with the indicated number of organisms in 0.1 ml saline IP.

TABLE 7

Protection of mice by IP immunization with alkali treated PS or alkali treated LPS to IP challenge with IT-1 P. aeruginosa

| Antigen | Amount given (ug) | Challenge dose (LD$_{50}$) | No. of Organisms | No. Survivors Total | % Protected |
|---|---|---|---|---|---|
| alkali PS | 250 | 10 | $1.2 \times 10^8$ | 0/8 | 0 |
| alkali PS | 50 | " | " | 0/8 | 0 |
| PS | 50 | " | " | 7/8 | 87.5 |
| — | 0 | " | " | 0/8 | 0 |
| alkali LPS | 0.05 | 20 | $5.0 \times 10^8$ | 10/10 | 100 |
| alkali LPs | 0.01 | " | " | 10/10 | 100 |
| LPS | 0.01 | " | " | 10/10 | 100 |
| alkali LPS + alkali PS | 50 | " | " | 8/10 | 80 |
| — | 0 | " | " | 0/10 | 0 |

Mice were immunized IP with the indicated amount of antigen in 0.1 ml saline and challenged IP 7 days later with the indicated amount of organisms in 0.1 ml saline.

Immunization of mice with the polysaccharide portion of LPS that eluted in the molecular weight 60,000 range was much less effective and only protected 30% of the challenged mice. Alkali treatment of these antigens destroyed all immunogenic capabilities.

Immunotype strains 2 through 7 of P. aeruginosa were also evaluated according to the above described procedure. The chemical compositions of polysaccharides isolated from immunotypes 2-7 were found to be virtually identical to that of immunotype 1. The chemical compositions were found to be 70% carbohydrate and 25-30% water, as determined by quantitative gas liquid chromatography and weighing after drying. Contamination with nucleic acids and protein was generally below 1% following the isolation procedure of this invention. There was found to be no detectable phosphate or lipid, nor any intact LPS.

Monosaccharide (sugar) compositions of the polysaccharides obtained from P. aeruginosa immunotypes 2 through 7 were also calculated. Table 8 below lists these compositions against an arbitrary value of 1.00 for glucose.

TABLE 8

Monosaccharide Composition (Moles/Mole Glucose) of Polysaccharide Antigens From *P. Aeruginosa* Immunotypes 2-7

| Polysaccharide Antigen From: | Monosaccharide | | | | | | | |
|---|---|---|---|---|---|---|---|---|
| | arabinose | rhamnose | xylose | mannose | galactose | glucose | 2-acetamido-2,6-dideoxy-galactose | 2 acetamido 2 deoxy glucose |
| Immunotype 2 | 1.56[a] | — | — | 1.91 | 3.89 | 1.00 | ++[b] | 0.22 |
| Immunotype 3 | 1.00 | 1.86 | 0.11 | 0.46 | 1.60 | 1.00 | ++ | — |
| Immunotype 4 | 0.32 | 0.02 | — | 1.45 | 0.38 | 1.00 | ++ | — |
| Immunotype 5 | 0.11 | 0.22 | — | 0.96 | 0.29 | 1.00 | ?[c] | — |
| Immunotype 6 | 0.10 | 0.08 | — | 3.44 | 1.05 | 1.00 | — | — |
| Immunotype 7 | 0.55 | 0.08 | — | 4.13 | 1.54 | 1.00 | ++ | — |

[a]represents moles per mole of glucose present
[b]2-acetamido-2,6-dideoxy galactose is unavailable as a standard and can only be identified as present (++) or absent (−) based on identification by mass spectroscopy
[c]? may be present, as yet undetermined The molecular weights for the immunotypes 2-7, as determined by chromatography on Sepharose CL-6B molecular sieve gels were found to range between $1.4 \times 10^5$ and $2.2 \times 10^5$ daltons. The polysaccharides from immunotypes 2-7 were found to be non pyrogenic in a standard rabbit pyrogenicity test at a level of 25 ugm polysaccharide per kilogram rabbit body weight.

A 10-25 ugm dose of PS from immunotypes 2, 3, 5, and 7 provided protection in mice to challenge with 5-40 50% lethal dose units ($LD_{50}$) of the homologous organism. Two doses of 10-25 ugm of PS from immunotype 6 provided protection against challenge with 5-40 $LD_{50}$ units of immunotype 6 organisms.

Two doses of 50 ugm of PS from immunotype 4 were found to protect against the challenge with 10 $LD_{50}$ units of immunotype 4 organisms.

A single 30 ugm dose of PS from immunotype 2, 3, 5, and 7, two 30 ugm doses of PS from immunotype 6, and two 50 ugm doses of PS from immunotype 4 were found to induce protection against challenge with live organisms from all seven immunotypes, as shown on Table 9 below.

TABLE 9

Protection of mice against challenge with live *P. aeruginosa* organisms, immunotype 1-7, when immunized with polysaccharide from *P. aeruginosa* immunotypes 1-7

| Challenge with live organisms of: | Immunized with Polysaccharide From Immunotype: | | | | | | | #LD 50's given | #live organisms given |
|---|---|---|---|---|---|---|---|---|---|
| | 1 | 2 | 3 | 4 | 5 | 6 | 7 | | |
| Immunotype 1 | 100[a] | 90 | 40 | 10 | 80 | 10 | 40 | 10 | $1.2 \times 10^8$ |
| Immunotype 2 | 60 | 80 | 50 | 0 | 30 | 20 | 20 | 8 | $8.3 \times 10^7$ |
| Immunotype 3 | 80 | 100 | 80 | 0 | 100 | 20 | 80 | 10 | $1.4 \times 10^6$ |
| Immunotype 4 | 10 | 60 | 20 | 60 | 30 | 10 | 10 | 15 | $4.4 \times 10^8$ |
| Immunotype 5 | 80 | 80 | 80 | 100 | 90 | 100 | 80 | 15 | $1.6 \times 10^7$ |
| Immunotype 6 | 30 | 20 | 40 | 50 | 30 | 90 | 60 | 18 | $6.2 \times 10^7$ |
| Immunotype 7 | 70 | 60 | 30 | 80 | 30 | 100 | 80 | 10 | $1.4 \times 10^7$ |

[a]percent survivors. Mice were given 30 ugm of polysaccharide from immunotypes 1, 2, 3, 5, and 7 IP and challenged 7 days later with live organisms IP. Immunizations with polysaccharides from immunotypes 4 and 6 were given on day 1 and 5 with challenge on day 12. Protection of 50% or more is significant at a level of 0.01 (Chi squared test)

In summary then, it has been discovered that a non toxic, non pyrogenic antigen can be isolated from the crude slime of *P. aeruginosa* strains, which antigen will induce immunity to challenge by the live organisms in a host. By eliminating the contaminating nucleic acids and LPS the PS isolated provides immunity without undesirable side effects or toxicity found in prior attempts to induce immunity against *P. aeruginosa* strains.

The invention may be embodied in other specific forms without departing from the spirit or essential characteristics thereof. The present embodiments are therefore to be consideration in all respects as illustrative and not restrictive, the scope of the invention being indicated by the appended claims rather than by the foregoing description, and all changes which come within the meaning and range of equivalency of the claims are therefore intended to be embraced herein.

What is claimed and desired to be secured by U.S. Letters Patent is:

1. Method for isolating a nontoxic, nonpyrogenic polysaccharide antigen from the crude slime of Pseudomonas aeruginosa comprising the steps of:
   a. adding about 1% by volume of a 10% cetyltrimethylammonium bromide solution to said slime to form a mixture which is allowed to stand for about 30 minutes to permit precipitation of nucleic acids;
   b. removing the nucleic acids precipitated in step a. by centrifugation;
   c. adding about 80% by volume of a 95% ethanol to the product of step b. to cause precipitation;
   d. collecting the precipitate formed in step c. by centrifugation and dissolving it in phosphate buffered saline;
   e. subjecting the product formed in step d. to the same treatment given to said slime by repeating steps a., b. and c. then collecting a second precipitate in the manner provided for in step d.;
   f. subjecting the precipitate collected in step e. to acetic acid hydrolysis followed by heating at around 90° C. for about 18 hours and allowing to cool to room temperature;
   g. centrifuging the cooled product formed in step f. to separate the lipid polysaccharides from the acetic acid supernate;
   h. extruding the acetic acid supernate formed in step g. with chloroform to remove residual lipid polysaccharides;
   i. subjecting the polysaccharides products formed in step h. to alcoholysis to precipitate the polysaccharides from the aqueous layer and separating said polysaccharides by centrifugation;
   j. dissolving the polysaccharide products in phosphate buffered saline, digesting with nucleases to remove nucleic acids and extracting the remaining protein therefrom with phenol;

k. mixing the polysaccharide product of step j., cooling and maintaining at a temperature of 4° C. for about 12 hours;
l. centrifuging the product of step k. to separate and remove the aqueous layer from the phenol layer;
m. subjecting the water layer formed in step l. to alcoholysis and separating the polysaccharides from the aqueous layer by centrifugation;
n. dissolving the polysaccharides of step m. in phosphate buffered saline and applied to a 2.6×100 cm column of Sephadex G-100 equilibrated in phosphate buffered saline;
o. combining the void volume fractions and subjecting to alcoholysis to precipitate the polysaccharides; and
p. isolating the polysaccharides having a molecular weight of from 100,000 to 300,000 daltons in the void volume by dissolving the polysaccharides of step o. in water and desalting on a 1.5×60 cm column of Sephadex G-50 equilibrated with a liquid selected from the group of distilled water and phosphate buffered saline having a pH of about 7.2.

2. The process of claim 1 wherein the liquid in step p. is phosphate buffered saline having a pH of about 7.2.

3. Method of inducing immunity in a host to challenge by Pseudomonas aeruginosa organisms by inoculating said host with a therapeutically effective amount of polysaccharide antigen prepared according to claim 1.

4. The method of claim 3 wherein the host is inoculated successively with at least 5 days between the first and second inoculation.

5. The product prepared according to the process of claim 1.

* * * * *